(12) United States Patent
Bartel et al.

(10) Patent No.: US 9,291,566 B2
(45) Date of Patent: Mar. 22, 2016

(54) STABLE INDIUM-CONTAINING SEMICONDUCTOR NANOCRYSTALS

(71) Applicant: LIFE TECHNOLOGIES CORPORATION, Carlsbad, CA (US)

(72) Inventors: Joseph Bartel, Carlsbad, CA (US); Yongfen Chen, Eugene, OR (US); Eric Tulsky, Berkeley, CA (US); Joseph Treadway, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/170,349

(22) Filed: Jan. 31, 2014

(65) Prior Publication Data

US 2014/0206096 A1 Jul. 24, 2014

Related U.S. Application Data

(62) Division of application No. 13/002,035, filed as application No. PCT/US2009/049517 on Jul. 2, 2009, now Pat. No. 8,679,543.

(60) Provisional application No. 61/077,832, filed on Jul. 2, 2008.

(51) Int. Cl.
| | |
|---|---|
| *A61K 9/14* | (2006.01) |
| *G01N 21/64* | (2006.01) |
| *B82Y 5/00* | (2011.01) |
| *B82Y 15/00* | (2011.01) |
| *C01B 25/08* | (2006.01) |

(Continued)

(52) U.S. Cl.
CPC .............. *G01N 21/6486* (2013.01); *B82Y 5/00* (2013.01); *B82Y 15/00* (2013.01); *C01B 25/082* (2013.01); *C09K 11/02* (2013.01); *C09K 11/565* (2013.01); *C09K 11/70* (2013.01); *C30B 7/00* (2013.01); *C30B 29/40* (2013.01); *C30B 29/48* (2013.01); *C30B 29/60* (2013.01); *G01N 33/588* (2013.01); *H01L 21/02601* (2013.01); *H01L 33/06* (2013.01); *H01L 21/02392* (2013.01); *H01L 21/02557* (2013.01); *H01L 21/02628* (2013.01)

(58) Field of Classification Search
CPC ..................................................... C01B 25/082
See application file for complete search history.

(56) References Cited

U.S. PATENT DOCUMENTS

| | | |
|---|---|---|
| 5,505,928 A | 4/1996 | Alivisatos et al. |
| 5,990,479 A | 11/1999 | Weiss et al. |

(Continued)

FOREIGN PATENT DOCUMENTS

| | | |
|---|---|---|
| WO | WO-2005/00207 | 1/2005 |
| WO | WO-2005/110916 | 11/2005 |

OTHER PUBLICATIONS

Battaglia, D. et al., "Formation of High Quality InP and InAs Nanocrystals in a Noncoordinating Solvent", 2002, 1027-1030.

(Continued)

*Primary Examiner* — Paul Dickinson
(74) *Attorney, Agent, or Firm* — Life Technologies Corporation

(57) ABSTRACT

Nanocrystals having an indium-based core and methods for making them and using them to construct core-shell nanocrystals are described. These core-shell nanocrystals are highly stable and provide higher quantum yields than known nanocrystals of similar composition, and they provide special advantages for certain applications because of their small size.

11 Claims, 1 Drawing Sheet

(51) Int. Cl.

| | | |
|---|---|---|
| *C30B 7/00* | (2006.01) | |
| *C30B 29/40* | (2006.01) | |
| *C30B 29/48* | (2006.01) | |
| *C30B 29/60* | (2006.01) | |
| *G01N 33/58* | (2006.01) | |
| *H01L 33/06* | (2010.01) | |
| *C09K 11/02* | (2006.01) | |
| *C09K 11/56* | (2006.01) | |
| *C09K 11/70* | (2006.01) | |
| *H01L 21/02* | (2006.01) | |

(56) References Cited

U.S. PATENT DOCUMENTS

| | | | |
|---|---|---|---|
| 6,114,038 A | 9/2000 | Castro et al. | |
| 6,207,392 B1 | 3/2001 | Weiss et al. | |
| 6,251,303 B1 | 6/2001 | Bawendi et al. | |
| 6,274,323 B1 | 8/2001 | Bruchez et al. | |
| 6,306,610 B1 * | 10/2001 | Bawendi et al. | 435/7.1 |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,426,513 B1 | 7/2002 | Bawendi et al. | |
| 6,500,622 B2 | 12/2002 | Bruchez, Jr. et al. | |
| 6,576,291 B2 | 6/2003 | Bawendi et al. | |
| 6,649,138 B2 | 11/2003 | Adams et al. | |
| 6,815,064 B2 | 11/2004 | Treadway et al. | |
| 7,767,260 B2 | 8/2010 | Peng et al. | |
| 2006/0157720 A1 | 7/2006 | Bawendi | |
| 2007/0049765 A1 | 3/2007 | Lucey et al. | |
| 2009/0264668 A1 | 10/2009 | Tokumitsu | |

OTHER PUBLICATIONS

Borchert, H et al., *Nano Letters*; vol. 2, Feb. 13, 2002, 151-154.
Haubold, S et al., *ChemPhysChem*; vol. 5, May 15, 2001, 331-334.
Langof, L et al., *Chemical Physics*; vol. 297, Feb. 16, 2004, 93-98.
Narayanaswamy, A et al., *Journal of Physical Chemistry C*; vol. 112, May 1, 2008, 6775-6780.
Xu, S. et al., "Rapid synthesis of highly luminescent InP and InP/ZnS nanocrystals", *J. Mater. Chem.*, vol. 18, 2008, pp. 2653-2656.
PCT/US09/49517, , "International Preliminary Report on Patentability Mailed Jan. 13, 2011".
PCT/US09/49517, , "International Search Report mailed Feb. 17, 2010", 14.
Xu, S. et al., "Rapid synthesis of highly luminescent InP and InP/ZnS nanocrystals", (electronic supplementary information), J. Mater. Chem., 2015, pp. 1-5.

* cited by examiner

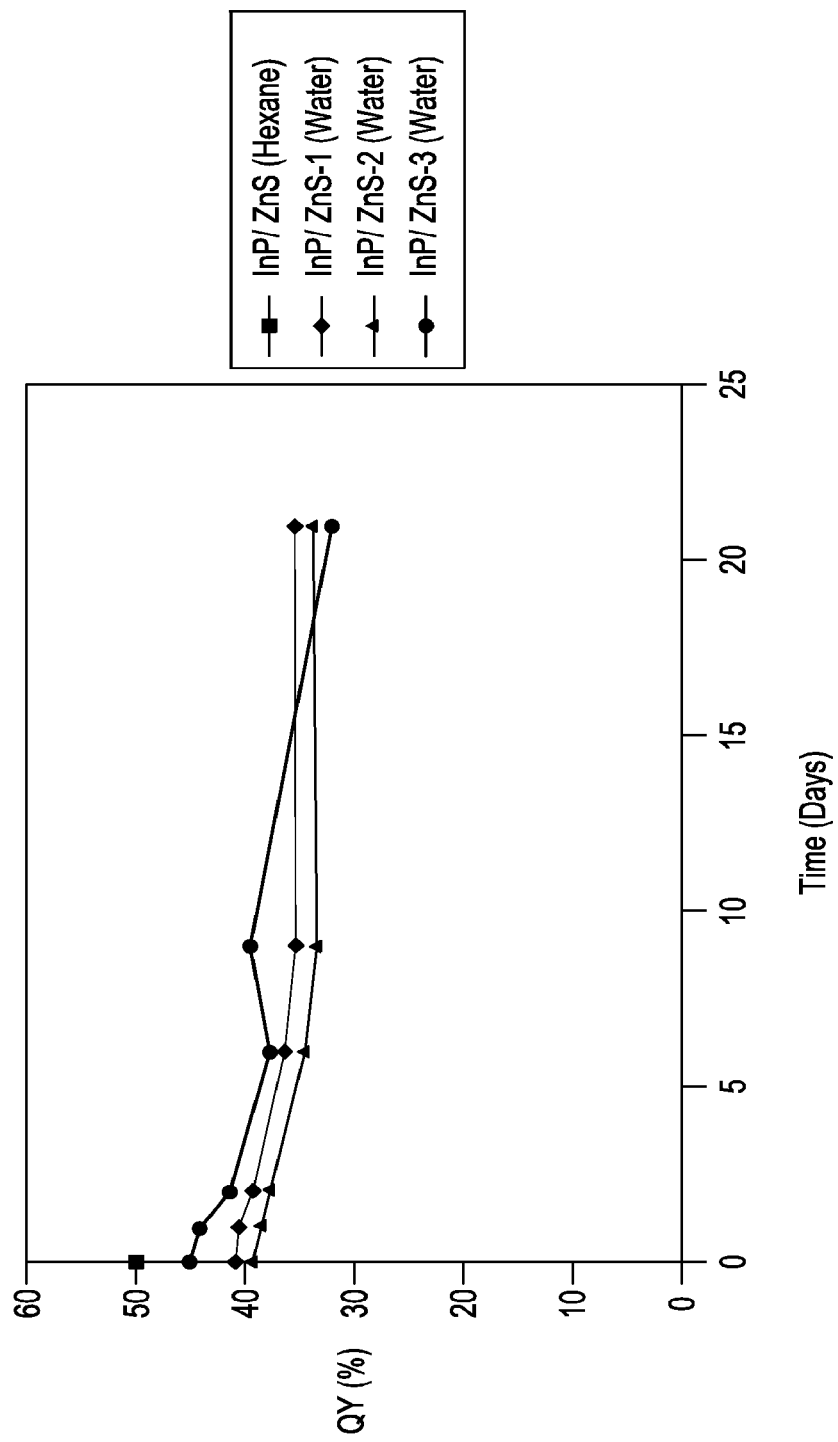

STABLE INDIUM-CONTAINING SEMICONDUCTOR NANOCRYSTALS

CROSS-REFERENCE TO RELATED APPLICATIONS

This application is a Division of U.S. application Ser. No. 13/002,035, filed on Jun. 1, 2011, now U.S. Pat. No. 8,679,543, which is a National Stage Application, filed under 35 USC 371 of International Application No. PCT/US2009/049517, filed Jul. 2, 2009, which claims priority to U.S. Provisional Patent Application No. 61/077,832, filed Jul. 2, 2008, the disclosures of which are hereby incorporated by reference in their entirety.

STATEMENT OF RIGHTS TO INVENTIONS MADE WITH FEDERALLY SPONSORED RESEARCH FUNDING

This invention was funded in part by the U.S. Government under Grant No. 70NANB4H3053 awarded by National Institute of Standards and Technology (NIST) Advanced Technology Program (ATP). The government may have certain rights in this invention.

FIELD OF THE INVENTION

Semiconductor nanocrystal compositions containing indium and methods of making and using such compositions are described.

DESCRIPTION OF RELATED ART

Semiconductor nanocrystals are photoluminescent particles that have a wide variety of applications. Semiconductor nanocrystals are sometimes referred to as quantum dots. Herein, the term 'quantum dot' is used to describe a semiconductor nanocrystal (e.g., core/shell nanocrystal).

Of the many unique properties of these materials, the photophysical characteristics may be the most useful. Specifically, these materials can absorb light and then emit an intense fluorescent emission of a wavelength that is particle size-dependent and particle composition-dependent. This fluorescent emission can have an extremely narrow luminescence bandwidth. Quantum dots are resistant to photobleaching under intensive light sources. Quantum dots can be efficiently excited with electromagnetic radiation having a shorter wavelength than the highest energy emitter in the material, and by varying the size and composition of the nanocrystal, a user can use many different types of nanoparticles mixed together and can still distinguish each type. These properties allow semiconductor nanocrystals to be used as markers or as ultrasensitive luminescent reporters of biological states and processes in highly multiplexed systems.

Nanocrystals used in biological applications typically have a central core, a surrounding shell, and optional capping groups, linkers, and other surface-conjugated materials. Typically, nanocrystals are described according to the composition of the core and of the semiconductor shell applied outside the core. The nanocrystal core largely determines its critical light absorption and emission characteristics. Nanocrystal cores have been broadly studied and improvements in synthesis have led to the optimization of key physiochemical properties resulting in nanocrystal cores with uniform size distributions and intense, narrow emission bands following photo-excitation. However, nanocrystal cores alone lack sufficiently intense or stable emission intensities for most applications, and nanocrystal cores are particularly sensitive to their environment; for example, the aqueous environment required for many biological applications can lead to the complete destruction of the luminescence of nanocrystal cores. Thus, methods to photostabilize nanocrystal cores (e.g., protect their luminescent properties) and make them stable and useful in aqueous media are of great interest for biological applications. Commonly, this is achieved by applying a shell over the core, to form a so-called core/shell nanocrystal. The shell usually stabilizes the nanocrystal and protects its photophysical properties. It may also provide an attachment surface for linking the nanocrystal to a molecule, cell, subcellular organelle, or the like that is to be tracked or observed.

The ability to coat nanocrystal cores has been an area of much research, and coating nanocrystal cores with an inorganic shell to form "core/shell nanocrystals," has resulted in improved emission intensity, chemical and photochemical stability, reduced self-quenching characteristics, stability in a variety of environments, and the like. The impact of coating nanocrystal cores with an inorganic shell on underlying luminescence energies is not well understood and is generally controlled based on a small set of criteria such as, for example, the choice of the coating material and the density and thickness of the shell. Optionally, an organic or other overcoat that is selected to provide compatibility with a dispersion medium may be applied to the shell on part or most of its surface; this overcoat is useful to adapt the inorganic particle to be soluble in or readily dispersed in a medium of choice, which may be aqueous or organic, hydrophilic or hydrophobic.

The inorganic shell is generally thought to passivate the outermost surface of a core nanocrystal thereby reducing or eliminating the surface energy states associated with the core and insulating the core from the outside environment. This can reduce or eliminate the nonradiative loss of excitons from the core to the environment, preserving the efficient fluorescence properties that a core can possess. Photochemical degradation may also be reduced, and emissions efficiency and stability may be improved, by coating a core with an inorganic shell.

The choice of shell material must be made to match the core material. For example, the shell material may generally have a wider band gap than the core, which enables it to protect the activated state that the core occupies when it has been photoactivated, forming a separated electron and hole. The shell may ideally be chosen to have an atomic spacing and lattice structure that closely match those of the core material to best preserve the photophysical attributes of the core, since irregularities in the interface between core and shell may be responsible for non-radiative energy dissipation mechanisms that reduce luminescent efficiency.

Core/shell nanocrystals having a CdX core wherein X is S, Se, or Te coated with a YZ shell where Y is Cd or Zn, and Z is S, Se, or Te are commonly produced and used, and have been shown to have good emission characteristics and stability. This may largely be due to the YZ coating material's bandgap energy which spans that of the core relatively symmetrically. 'Symmetry' as used in this sense means that the wider bandgap of the shell material fully encompasses the narrower bandgap of the core material and extends both above the high end of the core material's bandgap and below the low end of the core material's bandgap.

It must also be recognized that the bandgaps used to describe the core and shell materials are typically values that have been measured for and are characteristic of the bulk material; they may not represent the bandgap for the same material in a nanocrystal. The bandgap for a material is known to change as the size of the sample of the material changes. This is an underlying basis for the uniquely valuable fluorescence properties of nanocrystals, for example. It is not well understood how the bandgaps of various materials or mixtures of materials are affected as the sample approaches nanocrystal dimensions. In particular, a thin layer of a semiconductor material forming a shell on a nanocrystal may not have bandgap properties that are predictable relative to its bulk properties. Thus, while the bulk material properties can be useful to explain why certain pairs of materials work well, they may not be reliable for predicting which pairings of materials will work well.

One limitation of CdSe nanocrystals for certain applications like in vivo imaging or diagnostic tests is toxicity: Cadmium is considered a toxic metal. The toxicity of cadmium, and to a lesser extent selenium, raises concerns about using a nanocrystal containing cadmium and selenium for in vivo applications in live organisms or in living cells. Therefore, bright and stable nanocrystals that do not contain cadmium have special value for such uses, and for any use involving large scale production or use of nanocrystals, in order to minimize environmental impacts and associated health concerns.

Accordingly, for certain applications it is advantageous to use different core materials that do not have attendant toxicity concerns. Additionally, for some applications, very small or very large nanocrystals (relatively speaking) may be advantageous. For example, if used to label a biomolecule like DNA or a protein, it may be preferable to have a very small nanocrystal, less than about 10 nm in overall size, including the core/shell nanocrystal and a coating used on the shell to adapt the particle for use in a suitable medium. For biomolecules, the most relevant medium is frequently water; thus the nanocrystals must often be specially treated and/or coated so they are readily suspended or dissolved in water. For other applications, like tracking a large cell such as a bacterium, it may be advantageous to use a single, very bright nanoparticle, which would typically be a much larger particle. These nanocrystals may be particularly useful in certain in vivo applications where toxicity concerns are paramount, and in applications where visualizing a labeled molecule is important, and where a single small nanocrystal is least intrusive.

Many patents and patent publications report nanocrystal compositions, methods for their preparation, and methods for their use. The following is a sample of the research done to date.

U.S. Pat. No. 5,505,928 (issued Apr. 9, 1996) describes methods of preparing III-V semiconductor nanocrystal materials. Examples of such materials include GaAs, GaP, GaAs—P, GaSb, InAs, InP, InSb, AlAs, AlP, and AlSb. The produced materials can be 1-6 nm in size, and are relatively monodisperse.

U.S. Pat. No. 5,990,479 (issued Nov. 23, 1999) describes nanocrystals linked to affinity molecules. Listed affinity molecules include monoclonal and polyclonal antibodies, nucleic acids, proteins, polysaccharides, and small molecules such as sugars, peptides, drugs, and ligands.

U.S. Pat. No. 6,114,038 (issued Sep. 5, 2000) describes water soluble, functionalized nanocrystals having a capping compound of the formula $HS(CH_2)_nX$, wherein X is a carboxylate. The nanocrystals also have a diaminocarboxylic acid which is operably linked to the capping compound.

U.S. Pat. No. 6,207,229 (issued Mar. 27, 2001) describes a coated nanocrystal capable of light emission which includes a substantially monodisperse nanoparticle selected from the group consisting of CdX, where X=S, Se, or Te; and an overcoating of ZnY, where Y=S, or Se. Methods of preparing the nanocrystals using a first semiconductor core and a precursor capable of thermal conversion into a second semiconductor material that forms a coating layer over the core are also presented.

U.S. Pat. No. 6,207,392 (issued Mar. 27, 2001) describes semiconductor nanocrystals having one or more attached linking agents. The nanocrystals can include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs.

U.S. Pat. No. 6,251,303 (issued Jun. 26, 2001), U.S. Pat. No. 6,319,426 (issued Nov. 20, 2001) and U.S. Pat. No. 6,444,143 (issued Sep. 3, 2002) describe a water-soluble semiconductor nanocrystal. The outer layer of the nanocrystal contains a molecule having at least one linking group for attachment of the molecule to the overcoating shell layer, and at least one hydrophilic group optionally spaced apart from the linking group by a hydrophobic region sufficient to prevent electron charge transfer across the hydrophobic region.

U.S. Pat. No. 6,274,323 (issued Aug. 14, 2001) describes a method of detecting a polynucleotide in a sample, using a semiconductor nanocrystal in an immunosorbent assay.

U.S. Pat. No. 6,306,610 (issued Oct. 23, 2001) describes semiconductor nanocrystals having attached multidentate ligands. The nanocrystals can be associated with various biological molecules such as proteins and nucleic acids.

U.S. Pat. No. 6,322,901 (issued Nov. 27, 2001) describes monodisperse coated nanocrystals that emit light in a fluorescence band that is less than about 60 nm full width at half max (FWHM). The spectral range of the nanocrystals is about 470 nm to about 620 nm, and the particle size of the nanocrystal core is about 20 angstroms to about 125 angstroms.

U.S. Pat. No. 6,326,144 (issued Dec. 4, 2001) describes semiconductor nanocrystals linked to various compounds using a linker of structure $H_zX((CH_2)_nCO_2H)_y$, and salts thereof, where X is S, N, P or O=P; n is greater than or equal to 6; and z and y are selected to satisfy the valence requirements of X.

U.S. Pat. No. 6,423,551 (issued Jul. 23, 2002) and U.S. Pat. No. 6,699,723 (issued Mar. 2, 2004) describe a water soluble semiconductor nanocrystal having a linking agent capable of linking to an affinity molecule. A list of affinity molecules includes monoclonal and polyclonal antibodies, nucleic acids (both monomeric and oligomeric), proteins, polysaccharides, and small molecules such as sugars, peptides, drugs, and ligands. Examples of linking agents include N-(3-aminopropyl)-3-mercapto-benzamide, 3-aminopropyl-trimethoxysilane, 3-mercaptopropyltrimethoxysilane, 3-maleimidopropyl-trimethoxysilane, and 3-hydrazidopropyltrimethoxysilane.

U.S. Pat. No. 6,426,513 (issued Jul. 30, 2002) describes a water-soluble semiconductor nanocrystal comprising a nanocrystal core having a selected band gap energy; an overcoating layer comprising a material having a band gap energy greater than the band gap energy of the core; and an outer layer comprising a compound having a formula, $SH(CH_2)_nX$, where X is carboxylate or sulfonate, and n is greater than or equal to 8.

U.S. Pat. No. 6,500,622 (issued Dec. 31, 2002) describes semiconductor nanocrystals having attached polynucleotide sequences. The nanocrystals can be used to determine the presence or absence of a target sequence in a sample. The nanocrystal can be identified using a spectral code.

U.S. Pat. No. 6,548,168 (issued Apr. 15, 2003) describes a method of stabilizing particles with an insulating, semiconducting and/or metallic coating. A particle-coating admixture containing a bifunctional ligand is used to bind a particle to the coating. Examples of bifunctional ligands include 3-mercaptopropyl trimethoxysilane ("MPS"), 1,3-propanedithiol, 3-aminopropanethiol ("APT"), and 3-amino propyl trimethoxysilane ("APS").

U.S. Pat. No. 6,576,291 (issued Jun. 10, 2003) describes a method of manufacturing a nanocrystallite, the method comprising contacting a metal, M, or an M-containing salt, and a reducing agent to form an M-containing precursor, M being Cd, Zn, Mg, Hg, Al, Ga, In, or Ti; contacting the M-containing precursor with an X donor, X being O, S, Se, Te, N, P, As, or Sb to form a mixture; and heating the mixture in the presence of an amine to form the nanocrystallite. The nanocrystallites can be used in a variety of applications including optoelectronic devices including electroluminescent devices such as light emitting diodes (LEDs) or alternating current thin film electroluminescent devices (ACTFELDs).

U.S. Pat. No. 6,649,138 (issued Nov. 18, 2003) describes a water-dispersible nanoparticle comprising: an inner core comprised of a semiconductive or metallic material; a water-insoluble organic coating surrounding the inner core; and, surrounding the water-insoluble organic coating, an outer layer comprised of a multiply amphipathic dispersant molecule, wherein the dispersant molecule comprises at least two hydrophobic regions and at least two hydrophilic regions. The nanoparticles can be conjugated to various affinity molecules, allowing use in applications such as fluorescence immunocytochemistry, fluorescence microscopy, DNA sequence analysis, fluorescence in situ hybridization (FISH), fluorescence resonance energy transfer (FRET), flow cytometry (Fluorescence Activated Cell Sorter; FACS) and diagnostic assays for biological systems.

U.S. Pat. No. 6,815,064 (issued Nov. 9, 2004) describes a nanoparticle containing a Group 2 element, a Group 12 element, a Group 13 element, a Group 14 element, a Group 15 element, a Group 16 element, Fe, Nb, Cr, Mn, Co, Cu, or Ni in an inorganic shell around the semiconductor core. The compositions and methods of preparation are proposed to facilitate the overgrowth of a high-quality, thick shell on a semiconductive core by compensating for the mismatching of lattice structures between the core and shell materials.

CdSe nanocrystals have become the standard for many applications. However, there exists a need for new nanocrystal cores and core/shell nanocrystals that provide different photophysical properties, and can thus be distinguished from known nanocrystals. Several references mention nanocrystals made with a core containing indium, for example, to modify the particle's properties. WO 2005/110916 describes nanoparticles containing InGaP nanocrystals, and says InP nanoparticles can be made similarly. However, these nanoparticles require a layer of metal atoms to be applied over the core before a shell is applied. This adds a step to the manufacturing process and also increases the chances for variability in the end product. WO 2005/00207 also describes production of nanocrystals having an InP core and a non-coordinating solvent for formation of a shell on the InP cores. Its method, however, begins with a trialkyl indium material rather than the more convenient indium salts, and uses a cumbersome step to convert the trialkyl indium into an indium salt.

SUMMARY

Nanocrystals are provided having a core that comprises a semiconductor containing indium and phosphorus (InP). Nanocrystal cores and methods for making them are described herein, as well as methods for stabilizing these cores with a passivating shell to form core/shell nanocrystals. In some embodiments, the core is made from indium and phosphorus under conditions selected to minimize or prevent incorporation of other elements into the core. In certain embodiments, the core consists essentially of InP. Use of InP as the material for the core provides nanocrystals that exhibit high quantum yields and are much smaller than CdSe cores emitting at the same wavelength. Described herein are small, bright and extremely stable and versatile nanocrystals, as well as convenient methods for making such nanocrystals. These nanocrystals are non-toxic, making them particularly useful in certain biological applications. Methods are described that are applicable to preparation of a variety of different core-shell nanocrystals having improved properties, and are illustrated by preparation of InP core nanocrystals having a ZnS shell. InP has been recognized as a suitable material for some nanocrystals. However, few reports of InP nanocrystal cores have achieved high quantum yield (>25%) that is needed for many applications, and few have achieved sufficient photostability and environmental stability for real-world applications. In particular, there are few reports of stable, bright (high quantum yield plus good light absorption) InP nanocrystals. The present InP nanocrystals are stable and usable in an aqueous environment. The core/shell nanocrystal can have a core of InP and a shell of ZnS and needs no interface layer between the core and shell to achieve the desired properties. The ZnS shell is thus applied directly onto and in contact with the InP core. Avoiding the need for an interface layer simplifies preparation of the nanocrystal and makes it easier to produce a desired nanocrystal consistently, because it removes a source of potential defects such as lattice mismatches.

In one aspect, a semiconductor nanocrystal is provided that includes a core consisting essentially of indium and phosphorus, and a shell consisting essentially of zinc and sulfur, wherein the shell is directly on the core, and the nanocrystal has a quantum yield of at least 25%. Particular embodiments are directed to a semiconductor nanocrystal that consists essentially of a core consisting essentially of indium and phosphorus, and a shell consisting essentially of zinc and sulfur, wherein the shell is directly on the core, and the nanocrystal has a quantum yield of at least 25%. The shell can be formed directly on the core using a shell-forming reaction mixture that does not contain phosphorus. Typically, the shell is formed in the presence of a coordinating solvent (e.g., alkylamine). The nanocrystals provided herein are devoid of highly toxic components (e.g., metals), and are, therefore, non-toxic to cells or tissue. The nanocrystals can have an initial quantum yield of over 40%, although higher quantum yields can be achieved, depending on selection of the solvent. For example, the nanocrystals can have a quantum yield of at least about 50% when dispersed in an organic solvent. The nanocrystal can provide an initial quantum yield of at least 25% and a quantum yield of at least about 25% when dispersed in hexanes and stored in hexanes for three weeks. The semiconductor nanocrystal can be modified for dispersal in an aqueous medium. For example, the nanocrystal can further comprise an AMP coating. In certain embodiments, the quantum yield of the semiconductor nanocrystal (or a population thereof) can be at least about 35% when dispersed in an aqueous medium. Certain nanocrystals exhibit an initial quantum yield of at least about 40% when dispersed in water. The nanocrystal can be further modified to include a member of a specific binding pair (e.g., an antibody, antigen, hapten, antihapten, biotin, avidin, streptavidin, IgG, protein A, protein G, drug receptor, drug, toxin receptor, toxin, carbohydrate, lectin, peptide receptor, peptide, protein receptor, protein, carbohydrate receptor, carbohydrate, polynucleotide binding protein, polynucleotide, DNA, RNA, aDNA, aRNA, enzyme, substrate, or combinations of these). Also provided herein is a coated nanocrystal that includes a nanocrystal as described herein and further comprises a surface layer, the layer comprising one or more of an alkyl phosphine, an alkyl phosphine oxide, an alkyl carboxylic acid or salt thereof (e.g., oleic acid or an oleate), or an alkylamine.

In another aspect, the semiconductor nanocrystal can be a member of a population. The population can be a substantially monodisperse population of particles. The semiconductor nanocrystals in the population can comprise a core consisting essentially of indium and phosphorus and a shell consisting essentially of zinc and sulfur, wherein the shell is directly on the core, the population of nanocrystals having a quantum yield of at least 25%. Alternatively, the semiconductor nanocrystals in the population consist essentially of a core consisting essentially of indium and phosphorus, and a shell consisting essentially of zinc and sulfur, wherein the shell is directly on the core, and the population of nanocrystals having a quantum yield of at least 25%.

In yet another aspect, compositions are provided including an InP semiconductor nanocrystal which is non-toxic to cells or tissue. The semiconductor nanocrystal-containing compositions can emit light in a wavelength range that is substantially non-absorbent to animal fluid, cells, or tissue. Thus, the composition can be for use in a biological assay or can be adapted for inserting into a mammalian body. The compositions are photochemically and chemically stable and can exhibit a quantum yield of 40% or greater (e.g., 50% or greater). Certain compositions include water-dispersible nanocrystals. For example, a water-stable semiconductor nanocrystal composition is provided that comprises a semiconductor nanocrystal composition. The nanocrystals include a water-stabilizing layer having a hydrophobic portion for interacting with the surface of the semiconductor nanocrystal and a hydrophilic portion for interacting with an aqueous medium.

In another aspect, various methods of making nanocrystal core and shells are described. A representative method for making a nanocrystal having a core consisting essentially of InP and a shell consisting essentially of ZnS includes contacting a phosphorus source with an indium source in a non-coordinating solvent to form an InP core; and contacting the InP core with a zinc source and a sulfur source, wherein the sulfur source is in a medium that comprises a coordinating solvent, to form a ZnS shell directly on the InP core. The non-coordinating solvent can be a hydrocarbon (e.g., 1-octadecene, squalane, octadecane, or tetradecane). In certain embodiments, the non-coordinating solvent consists essentially of a hydrocarbon. In certain embodiments, the non-coordinating solvent consists essentially of 1-octadecene. The sulfur source is typically added after the zinc source and can be gradually added over a period of 30 minutes or greater. The method can further include cleaning the InP core before applying the ZnS shell to it. The shell of ZnS can be formed by contacting the core of InP with a zinc source and sulfur in a medium that comprises an alkylamine (e.g., a $C_5$-$C_{15}$ alkylamine). The coordinating solvent can be a $C_5$-$C_{20}$ alkylamine. The medium further can comprise a hydrocarbon solvent such as 1-octadecene. In certain embodiments, the medium does not contain a phosphine or phosphine oxide. The method can benefit by rigorously excluding oxygen from the nanocrystal preparation until after the shell has been formed. The indium source can be an indium precursor such as a $C_5$-$C_{20}$ alkylcarboxylate salt of indium. The phosphorus source can be a phosphorus precursor such as a trialkylsilyl phosphine. The zinc source can be a zinc precursor such as a lipophilic zinc salt (e.g., a $C_5$-$C_{20}$ alkylcarboxylate salt of zinc). The sulfur source can be elemental sulfur. The sulfur source can be added slowly to a reaction mixture containing InP core nanocrystals and the zinc source, while the mixture is at a temperature above about 200° C. The method can be used to produce semiconductor nanocrystals having a ZnS shell thickness of at least 0.5 nm and an average diameter of about 20 nm or less. For example, the thickness of the ZnS shell can be about 1 nm.

In yet another aspect, a method to prepare an InP nanocrystal core is provided, comprising contacting an alkylcarboxylate salt of indium in a hydrocarbon solvent with a trialkylsilyl phosphine, in the absence of other phosphorus-containing species; heating the mixture at a temperature that induces nanocrystal formation; monitoring the nanocrystal formation to produce a desired nanoparticle size; and isolating the nanoparticles; wherein the process is conducted with rigorous exclusion of oxygen. The method produces a nanocrystal core that consists essentially of indium and phosphorous. The InP nanocrystal core can further comprise a surface coating of an alkyl carboxylic acid or salt thereof.

In yet another aspect, a method to grow a ZnS shell on a nanocrystal core is provided, comprising dispersing the nanocrystal core in a hydrocarbon solvent to form a mixture; heating the mixture to a temperature above 200° C.; and slowly adding sulfur admixed with an alkylamine to the heated mixture. Sulfur is typically added over a period of 30 minutes or more.

In yet another aspect, the methods provided herein can be used to prepare a population of nanocrystals. In certain embodiments, the population is substantially monodisperse. The population can have a peak emission wavelength ranging from about 500 nm to about 800 nm. The nanocrystals of the population can emit light in a spectral range that is about 70 nm or less at full width half maximum (FWHM).

The InP nanocrystals described herein possess a combination of properties that make them ideally suited for use in biological assays and in imaging applications. These InP nanocrystals exhibit a higher quantum yield than has been achieved with known InP nanocrystals. Further, these nanocrystal compositions are colloidally stable and do not lose quantum yield when exposed to air. These nanocrystals are stable toward dispersal and storage in water or organic solvent, as well as upon PEGylation or conjugation to a bioaffinity molecule. The exceptionally optical properties, coupled with their stability, make the disclosed nanocrystals ideally suited for biological applications (e.g., in vivo, flow cytometry or cellular imaging reagent). The nanocrystal compositions are also non-toxic to cells or tissue and are capable of emitting light in a wavelength range that is substantially non-absorbent to animal fluid, cells, or tissue. Tissue penetration can be further enhanced by use of InP nanocrystals having a small cross-sectional diameter. Due to this combination of attributes, the described nanocrystals can be used in medical compositions (e.g., diagnostic compositions for introduction into mammalian bodies).

Thus, in yet another aspect, a method of detecting a target in a sample is provided, the method comprising contacting a biological sample with a semiconductor nanocrystal (or a population thereof) or a nanocrystal composition as described herein, wherein the nanocrystal or composition is non-toxic to cells or tissues; and detecting the fluorescence emission of the semiconductor nanocrystal. Also provided is a method of detecting an interaction between a compound and a biological target, the method comprising providing a non-toxic composition capable of a characteristic spectral emission, the composition comprising a compound and a semiconductor nanocrystal as described herein associated with the compound, wherein the composition is non-toxic to cells or tissues, and wherein the emission provides information about a biological state or event; allowing a sample comprising a biological target to interact with the composition; and detecting interaction between the compound and the biological target by monitoring the spectral emission of the sample. The spectral emission can be associated with a variety of assays, such as immunochemistry, immunocytochemistry, immunobiology, or immunofluorescence assays; DNA sequence analyses; fluorescence resonance energy transfer, flow cytometry, or fluorescence activated cell sorting assay; diagnostics in biological systems, in vivo imaging, and high-throughput screening.

Although the InP nanocrystals provided herein are uniquely suited to biological applications, the described nanocrystals also could be utilized in many other non-biological applications, in particular those where environmental and/or health concerns are an issue.

DESCRIPTION OF THE FIGURES

The following FIGURE forms part of the present specification and is included to further demonstrate certain aspects of the present invention. The invention may be better understood by reference to this FIGURE in combination with the detailed description of specific embodiments presented herein.

FIG. 1 shows the fluorescence yield (quantum yield) for nanocrystals having InP cores and ZnS shells made by the methods described herein. These nanocrystals provided very high quantum yield initially after they were prepared, and they retained high quantum yields over prolonged time in hexanes or water, e.g., losing less than a third and typically less than a quarter of their initially high quantum yields. Even after three weeks in solution, the nanocrystals described herein provide a quantum yield of greater than 30%.

DETAILED DESCRIPTION OF THE INVENTION

While compositions and methods are described in terms of "comprising" various components or steps (interpreted as meaning "including, but not limited to"), the compositions and methods can also "consist essentially of" or "consist of" the various components and steps, unless otherwise clearly indicated herein. Such terminology should be interpreted as defining essentially closed-member groups.

DEFINITIONS

Unless defined otherwise, all technical and scientific terms used herein have the same meaning as is commonly understood by one of ordinary skill in the art to which this invention belongs.

As used herein, "a" or "an" means "at least one" or "one or more."

As used herein, "about" means that the numerical value is approximate and small variations would not significantly affect the practice of the invention. Where a numerical limitation is used, unless indicated otherwise by the context, 'about' means the numerical value can vary by ±10% and remain within the scope of the invention.

"Alkyl" as used in reference to alkyl phosphine, alkyl phosphine oxide, alkylcarboxylate or alkylamine refers to a hydrocarbon group having 1 to 20 carbon atoms, frequently between 4 and 15 carbon atoms, or between 6 and 12 carbon atoms, or between 5 and 20 carbon atoms, and which can be composed of straight chains, cyclics, branched chains, or mixtures of these. The alkyl phosphine, alkyl phosphine oxide, or alkylamine include embodiments having from one to three alkyl groups on each phosphorus or nitrogen atom. In preferred embodiments, the alkyl phosphine or alkyl phosphine oxide has three alkyl groups on P, and the alkyl amine(s) have one alkyl group on N. In some embodiments, the alkyl group contains an oxygen atom in place of one carbon of a $C_4$-$C_{15}$ or a $C_6$-$C_{12}$ alkyl group, provided the oxygen atom is not attached to P or N of the alkyl phosphine, alkyl phosphine oxide, or alkylamine. In some embodiments, the alkyl can be substituted by 1-3 substituents selected from halo and $C_1$-$C_4$ alkoxy. The alkyl groups herein can also include one-two unsaturated bonds (double bonds), provided those bonds do not include the carbon directly attached to P or N.

Preferred alkyl phosphines include compounds of the formula $[(C_4\text{-}C_{10})_3]P$. Preferred alkyl phosphine oxides include compounds of the formula $[(C_4\text{-}C_{12})_3]P=O$. Preferred alkylamines include compounds of formula $(C_4\text{-}C_{12})_2NH$ and $(C_4\text{-}C_{12})NH_2$, where each $C_4$-$C_{12}$ alkyl is a straight or branched chain unsubstituted alkyl group. Preferred alkyl phosphonic acids and alkyl phosphinic acids include those having 1-20 carbon atoms and preferably 6-15. Preferred alkyl carboxylates for use in the methods of the invention include $C_5$-$C_{20}$ alkyl groups with an attached carboxylic acid group, e.g., $(C_5\text{-}C_{20})$alkyl-COOH, where the alkyl can be straight chain, branched, cyclic or a combination of these.

"Hydrophobic" as used herein refers to a surface property of a solid, or a bulk property of a liquid, where the solid or liquid exhibits greater miscibility or solubility in a low-polarity medium than it does in a higher polarity medium. A nanocrystal that is soluble in organic solvents that are not miscible with water, such as ethyl acetate, dichloromethane, MTBE, hexane, or ether, is hydrophobic. By way of example only, nanocrystals that are soluble in a hydrocarbon solvent such as decane or octadecene and are insoluble in an alcohol such as methanol are hydrophobic.

"Hydrophilic" as used herein refers to a surface property of a solid, or a bulk property of a liquid, where the solid or liquid exhibits greater miscibility or solubility in a high-polarity medium than it does in a lower polarity medium. By way of example, a material that is more soluble in methanol than in a hydrocarbon solvent such as decane would be considered hydrophilic.

"Growth medium" or "medium" as used herein refers to a mixture of reagents and/or solvents in which a nanocrystals is grown or in which a shell is grown on a nanocrystals.

"Coordinating solvents" as used herein refers to a solvent such as TOP, TOPO, carboxylic acids, and amines, which are effective to coordinate to the surface of a nanocrystal. 'Coordinating solvents' include phosphines, phosphine oxides, phosphonic acids, phosphinic acids, amines, and carboxylic acids, which are often used in growth media for nanocrystals, and which form a passivating layer on the nanocrystal surface. They exclude hydrocarbon solvents such as hexanes, toluene, hexadecane, octadecene, and the like, which do not have heteroatoms that provide bonding pairs of electrons to coordinate with the nanocrystal surface. Hydrocarbon solvents that do not contain heteroatoms such as O, S, N or P to coordinate to a nanocrystal surface are referred to herein as non-coordinating solvents. Note that the term 'solvent' is used in its ordinary way in these terms: it refers to a medium that supports, dissolves, or disperses materials and reactions between them, and does not ordinarily participate in or become modified by the reactions of the reactant materials. Certain solvents, however, may participate in or become modified (e.g. TOP can be oxidized to TOPO).

"Luminescence" refers to the property of emitting electromagnetic radiation from an object. Typically, the electromagnetic radiation is in the range of UV to IR radiation and may refer to visible electromagnetic radiation, for example light. Luminescence may result when a system undergoes a transition from an excited state to a lower energy state resulting in the release of a photon. The transition responsible for luminescence can be stimulated through the release of energy stored in the system chemically or kinetically, or can be added to the system from an external source, such as, for example by a photon or a chemical, thermal, electrical, magnetic, electromagnetic, physical energy source, or any other type of energy source capable of exciting the system. In some embodiments, 'luminescence' refers to fluorescence—emission of a photon that is initiated by excitation with a photon of higher energy (shorter wavelength) than the emitted photon.

"Exciting a system" or "exciting" or "excitation" refers to inducing the energy state of a system into a higher state than that of ground state. The term "excitation wavelength" refers to electromagnetic energy which may have a shorter wavelength than that of the emission wavelength that is used to excite the system. The "energy states" of the system described herein can be electronic, vibrational, rotational, or any combination thereof. The term "emission peak" refers to the wavelength that has the highest relative intensity within a characteristic emission spectra.

The term "solid solution", as used herein, may refer to a compositional variation that is the result of the replacement of an ion or ionic group for another ion or ionic group, for example, CdS in which some of the Cd atoms have been replaced with Zn. In contrast, a "mixture" or "alloy", as used herein, may refer to a class of matter composed of two or more substances in which each substance retains its own identifying properties.

The term "monodisperse" refers to a population of particles having substantially identical size and shape. One of ordinary skill in the art will realize that particular sizes of nanocrystals, such as of semiconductor nanocrystals, are actually obtained as particle size distributions. For the purpose of the present invention, a "monodisperse" population of particles means that at least about 60% of the particles or, in some cases, about 75% to about 90% or more of the particles, fall within a specific particle size range, and the particles deviate in diameter or largest dimension by less than 20% rms (root-mean-square) deviation and, in some cases, less than 10% rms deviation, and, in some cases, less than 5% rms deviation. Certain monodisperse populations of nanocrystals are provided herein that have a rms deviation of less than about 20%. Other monodisperse populations of nanocrystals are provided herein that have a rms deviation of less than about 15%.

The term "semiconductor nanocrystal" or "nanocrystal" or "quantum dot" are used herein to refer to minute particles composed of a crystalline inorganic semiconductor material or mixture of materials. These nanocrystals are luminescent and are useful as fluorescent markers or labels that facilitate identifying, locating, tracking, or quantifying, etc. molecules, particles, cells and the like. A nanocrystal may include one or more shells or other coatings in addition to a semiconductor core, and then can be referred to as a core/shell nanocrystal.

A "core/shell nanocrystal" or "quantum dot" refers to a nanocrystal that includes a nanocrystal core of one or more first semiconductor materials contained within or substantially surrounded by a shell of a second inorganic material that is frequently a semiconductor, also. Preferably, the shell is a material chosen to have a bandgap width that is wider than the bandgap of the core, as described above.

In some embodiments, the invention provides a coated core/shell nanocrystal. The coating can comprise an organic material, such as a layer of TOP or TOPO or other coordinating ligands that can make the nanocrystal or quantum dot soluble in hydrophobic media, or a hydrophilic coating such as an AMP coating as discussed in U.S. Pat. No. 7,108,915, which provides a water-soluble or water dispersable composition. In certain embodiments, a population of coated nanocrystals (e.g., InP core or InP/ZnS core/shell) is provided, where the nanocrystals comprise a coating of a lipophilic carboxylic acid ligand. The lipophilic carboxylic acid can be a fatty acid. The fatty acid can have any size, however, fatty acid ligands containing about $C_4$-$C_{24}$ carbon atoms have been found to be particular useful in the practice of the invention although ligands having other chain lengths can be used. For example, the chain may comprise a saturated hydrocarbon, a monounsaturated hydrocarbon, or a polyunsaturated hydrocarbon. The hydrocarbon chain can further include a heavily branched or lightly branched hydrocarbon chain. One representative fatty acid ligand is oleic acid. Nanocrystals coated with other types of fatty acid ligands are also feasible and include, for example, butyric acid, caproic acid, caprylic acid, capric acid, lauric acid, myristic acid, palmitic acid, margaric acid, stearic acid, arachidic acid, behenic acid, lignoceric acid, myristoleic acid, palmitoleic acid, gadoleic acid, erucic acid, nervonic acid, linoleic acid, linolenic acid, parinaric acid, aracidonic acid, timnodonic acid, brassic acid, and clupanodonic acid.

The typical nanocrystal is comprised of a core and a shell. The terms "semiconductive core", "nanocrystal core", "core nanocrystal" or "core" refer to a nanocrystal composed of an inorganic semiconductive material, a mixture or solid solution of inorganic semiconductive materials, or an organic semiconductive material. Cores can be isolated, or can be partially or fully covered by a shell or shells.

The term "shell" refers to an inorganic semiconductive layer surrounding a nanocrystal core. An "inorganic shell", as described herein, is a shell composed of an inorganic material, or a mixture or solid solution of inorganic materials. A suitable shell provides insulating ability both above and below the bandgap of the core material. A suitable shell for a particular nanocrystal core will have a bandgap that is wider than the bandgap of the core, and that extends above the high end of the bandgap of the core and below the low end of the bandgap of the core. In certain embodiments, the inorganic shell may be composed of an insulating material or another semiconductive material. In some embodiments, the shell comprises magnesium and is referred to herein as a magnesium-containing shell. Some embodiments of the nanoparticles of the invention have a shell that comprises, or consists of, or consists essentially of, ZnS. In some embodiments, the shell comprises or consists essentially of a mixture of ZnS and MgS. Shells formed from ZnS and MgS can be prepared according to the methods that are well known to those skilled in the art and include those described in co-pending application number PCT/US08/65425.

The shell can vary in thickness but typically has a thickness of at least 0.5 nm. For example, the shell thickness can be about 0.1 nm or more; or about 1 nm or more; or about 5 nm or more. In certain embodiments, the shell thickness is about 3 nm or less or about 2 nm or less. Certain nanocrystals include a shell having about 3 monolayers of ZnS (e.g., about 1 nm). Thicker ZnS shells constructed of more than several monolayers (e.g., 5-10; or 10-15; or 15-20; or 20-30 monolayers) also can be produced by the methods described herein.

Nanoparticles can be synthesized in shapes of different complexity such as spheres, rods, discs, triangles, nanorings, nanoshells, tetrapods, and so on. Each of these geometries have distinctive properties: spatial distribution of the surface charge, orientation dependence of polarization of the incident light wave, and spatial extent of the electric field. In many embodiments, the nanocrystals of the invention are roughly spherical.

A typical single-color preparation of nanoparticles has crystals that are preferably of substantially identical size and shape. Nanocrystals are typically thought of as being spherical or nearly spherical in shape, but can actually be any shape. Alternatively, the nanocrystals can be non-spherical in shape. For example, the nanocrystal's shape can change towards oblate spheroids for redder colors. It is preferred that at least about 60%, at least about 70%, at least about 80%, at least about 90%, at least about 95%, and ideally about 100% of the particles are of the same size. Size variation can be measured as root mean square ("rms") deviation of the diameter, with less than about 20% root mean square deviation being preferred. Size variation can be less than about 10% rms deviation, less than about 9% rms deviation, less than about 8% rms deviation, less than about 7% rms deviation, less than about 6% rms deviation, less than about 5% rms deviation, or ranges between any two of these values. Such a collection of particles is sometimes referred to as being "monodisperse".

Generally, a nanocrystal is a semiconductive particle, having a diameter or largest dimension in the range of about 1 nm to about 100 nm, or in the range of about 2 nm to about 50 nm, and in certain embodiments, in the range of about 2 nm to about 20 nm or from about 2 to about 10 nm. In certain embodiments, the average diameter is 20 nm or less. More specific ranges of sizes include about 0.5 nm to about 5 nm, about 1 nm to about 50 nm, and about 1 nm to about 20 nm. Specific size examples include about 0.1 nm, about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm, and ranges between any two of these values. In some embodiments, a core nanocrystal less than about 10 nm in diameter, or less than about 7 nm in diameter, or less than about 5 nm in diameter. Certain nanocrystals provided herein have a diameter of about 4 nm. InP-containing nanocrystals of such a small size have been found to emit light at wavelengths that are considerably longer than for equivalently sized Group II-VI semiconductor nanocrystals, such as CdSe. For example, 4 nm InP/ZnS nanocrystals have an emission wavelength of about 600 nm, whereas a similarly sized CdSe nanocrystal typically emit at a wavelength of about 545 nm.

It is well known that the color (emitted light) of the semiconductor nanocrystal can be "tuned" by varying the size and composition of the nanocrystal. Nanocrystals preferably absorb a wide spectrum of wavelengths, and emit a narrow wavelength of light. The excitation and emission wavelengths are typically different, and non-overlapping. For a population of nanocrystals, the width of emission is preferably less than about 100 nm, and more preferably less than about 90 nm at full width at half maximum of the emission band (FWHM). Certain materials described herein have a width of emission of about 80 nm or less (FWHM), whereas other materials have a FWHM emission of about 70 or less or 60 nm or less. Examples of emission widths (FWHM) include about 70 nm, about 60 nm, about 50 nm, about 40 nm, about 30 nm, about 20 nm, and about 10 nm.

The emitted light preferably has a symmetrical emission of wavelengths. The emission maxima can generally be at any wavelength from about 200 nm to about 2,000 nm. For example, the nanocrystals provided herein can have a maximum emission wavelength within the range of about 450 nm to about 1000 nm. Examples of emission maxima include about 200 nm, about 400 nm, about 600 nm, about 800 nm, about 1,000 nm, about 1,200 nm, about 1,400 nm, about 1,600 nm, about 1,800 nm, about 2,000 nm, and ranges between any two of these values. Certain nanocrystals (e.g., InP/ZnS core/shell nanocrystals) have an emission maximum at about 550 nm to about 750 nm. Other nanocrystals have an emission maximum at about 550 nm to about 625 nm. A particular InP/ZnS nanocrystal has an emission maximum at about 600 nm, although InP/ZnS nanocrystals having other wavelengths can be prepared according to the methods provided herein, as well.

A specific type of a fluorescent semiconductor nanocrystal has an InP core and a ZnS shell. The InP/ZnS nanocrystal can be a member of a population. Because the core comprises indium and phosphorus and the shell zinc and sulfur, the resulting core-shell quantum dots are ideal for applications where cadmium toxicity is a concern. Examples of these nanocrystals prepared by the methods disclosed herein have been shown to be chemically, electrically, and photochemically stable in an aqueous or organic medium. Examples of these nanocrystals have been shown to be stable for many months in hexane, for example, and in other nonpolar solvents. They exhibit a quantum yield about 40% or higher in many embodiments. Examples of these nanocrystals have been coated with an amphiphilic polymeric coating that adapts them to be dispersed in water without a significant decrease in quantum yields, e.g., less than a 15% loss of quantum yield was seen after several months in water. These, too, are chemically and electrically stable for months. The InP/ZnS nanocrystals can also be PEGylated and conjugated to a bioaffinity molecule, e.g. avidin or streptavidin, with only slight loss of quantum yield, e.g., less than about 10% loss.

Advantageously, the nanocrystals of the invention have a quantum yield of at least about 30%, or at least about 35%. The quantum yield can change over time, and in some embodiments it does not decrease by more than 50% after three weeks in solution. Preferably, it does not decrease by more than about 35% over three weeks, and in some embodiments the quantum yield decreases by less than 25% over a period of three weeks in solution.

In one example, InP/ZnS nanocrystals disclosed herein provided a quantum yield of 50.7% when dispersed in hexanes. The same nanocrystals when coated with AMP (an amphiphilic polymer coating—see U.S. Pat. No. 7,108,915) and dispersed in water, provided a quantum yield of 39.8%. When kept in water for 21 days, the quantum yield of the AMP-coated nanocrystals had decreased only a little, to 35.5%. The same nanocrystals were PEGylated and conjugated with streptavidin, and still exhibited a quantum yield of 30.0%. After 40 days, these streptavidin-coated nanocrystals had a quantum yield of 25%. The stability of these nanocrystals is illustrated in FIG. 1.

The nanoparticles can have surface coatings adding various functionalities. For example, the nanocrystals can be coated with lipids, phospholipids, fatty acids, polynucleic acids, polyethylene glycol, primary antibodies, secondary antibodies, antibody fragments, protein or nucleic acid based aptamers, biotin, streptavidin, proteins, peptides, small organic molecules, organic or inorganic dyes, precious or noble metal clusters. An additional embodiment of the invention is directed towards nanoparticles coated with phospholipids. An example of such a nanocrystal is a commercially available phospholipid-coated Maple Red-Orange EVITAG-T2 nanocrystal (Evident Technologies; Troy, N.Y.). Other embodiments utilize an amphiphilic (AMP) polymer coating.

Spectral characteristics of nanoparticles can generally be monitored using any suitable light-measuring or light-accumulating instrumentation. Examples of such instrumentation are CCD (charge-coupled device) cameras, video devices, CIT imaging, digital cameras mounted on a fluorescent microscope, photomultipliers, fluorometers and luminometers, microscopes of various configurations, and even the human eye. The emission can be monitored continuously or at one or more discrete time points. The photostability and sensitivity of nanoparticles allow recording of changes in electrical potential over extended periods of time.

Additional methods of assaying the emission from the nanostructure include measuring changes in light intensity, light polarization, light absorption, color of the emission, emission lifetime or half-life, or the "blinking" pattern.

In one aspect, the invention provides a nanocrystal comprising a core that consists primarily or essentially of InP. In contrast to InP nanocrystals known in the art (e.g., InGaP), the present nanocrystals do not include additional elements or dopants, such as, for example, gallium, silicon, or zinc. In certain embodiments, the InP nanocrystals do not contain elemental dopants including TMS. The core can be made by methods described herein to achieve suitable quantum yields.

A representative method for preparing nanocrystals involves contacting a phosphorus source with an indium source in a non-coordinating solvent to form a core consisting essentially of InP. Alternatively, a coordinating solvent, such as trioctylphosphine, can be used in the preparation of the InP core. Coordinating solvents have been shown to be particularly useful in the preparation of near-IR emitting InP nanocrystals. The InP cores are then contacted with a zinc source and a sulfur source to form a shell consisting essentially of ZnS directly on the InP core. The sulfur source can be in a medium that comprises a coordinating solvent (e.g., a coordinating solvent other than a phosphine or phosphine oxide) and is usually added to the InP solution after the zinc source slowly (e.g., over a period of 30 minutes or more). These synthesis procedures should be conducted with special care to exclude moisture and oxygen, thus solvents and reagents were carefully purged of oxygen before mixing and all transformations were conducted under inert atmosphere (e.g., nitrogen or argon) throughout the process of forming the InP core and adding a shell to it. While not wishing to be bound by theory, it is thought that the rigorous exclusion of oxygen and water during the entire synthesis procedure contributes, at least in part, to the high quantum yield of the nanocrystals disclosed herein.

One exemplary method for preparing InP nanocrystal cores comprises contacting an alkylcarboxylate salt of indium in a hydrocarbon solvent with a trialkylsilyl phosphine, in the absence of other phosphorus-containing species; heating the mixture at a temperature that induces nanocrystal formation; monitoring the nanocrystal formation to produce a desired nanoparticle size; and isolating the nanoparticles, wherein the process is conducted with rigorous exclusion of oxygen. The InP nanocrystal cores prepared according to this method include a surface coating of an alkylcarboxylic acid (e.g., oleic acid) or a salt thereof.

In some embodiments, the core is prepared in a reaction mixture that does not contain any added phosphorus compounds, (phosphine or phosphine oxide or phosphonic or phosphinic acids, for example) other than the phosphorus source (e.g., a phosphorus precursor). The only source of phosphorus is typically the phosphorus precursor, which can be, for example, $(TMS)_3P$. The reaction to form the core is typically conducted in solvent that does not comprise any coordinating solvent components. The present methods typically do not use the coordinating solvents typically used in the preparation of Group II-VI nanocrystals, such as TOP, TOPO, and the like.

To solubilize the indium precursor in a non-coordinating solvent mixture, it may be helpful to use an indium salt of a lipophilic acid such as myristic acid or oleic acid, for example. Other $C_4$-$C_{24}$ carboxylic acids also can be used for this purpose (e.g., butyric acid, caproic acid, caprylic acid, capric acid, lauric acid, myristic acid, palmitic acid, margaric acid, stearic acid, arachidic acid, behenic acid, lignoceric acid, myristoleic acid, palmitoleic acid, gadoleic acid, erucic acid, nervonic acid, linoleic acid, linolenic acid, parinaric acid, aracidonic acid, timnodonic acid, brassic acid, and clupanodonic acid). These salts can be prepared by heating an indium salt such as indium acetate $(In(OAc)_3)$ in a non-coordinating solvent in the presence of a lipophilic acid such as oleic acid, myristic acid, or another $C_4$-$C_{24}$ hydrocarbyl carboxylic acids. Preferably, the mixture of indium salt and lipophilic carboxylic acid are heated under vacuum, or with an inert atmosphere flowing through the reaction vessel, so any volatiles produced in this reaction (e.g., acetic acid when using indium acetate and a higher-molecular weight lipophilic carboxylic acid) will be pulled or swept out of the reaction mixture. This reaction can be heated to facilitate formation of the lipophilic indium carboxylate salt and removal of byproducts. Once the indium precursor is combined with a non-coordinating solvent such as a hydrocarbon, a phosphorus source is added. Any hydrocarbon can be used in this step. However, in certain synthetic procedures (e.g., flow synthesis), it may be preferred to use a saturated hydrocarbon that is less susceptible to polymerization. Representative hydrocarbons include, e.g., 1-octadecene (ODE), octadecane, tetradecane, and squalane. Other suitable non-coordinating solvents for use in this step include hydrocarbons such as dodecane, squalane, and other saturated, monounsaturated, or polyunsaturated alkyl/alkenyl solvents that are reasonably stable under these reaction conditions. The phosphorus source can be added neat (without solvent), or it can be dissolved in a non-coordinating solvent. In some embodiments, the phosphorus source is a phosphorus precursor such as tris(trimethylsilyl)phosphine, or $TMS_3P$. Other trialkylsilyl phosphines can be used as well, e.g., triethylsilyl phosphine or t-butyldimethylsilyl phosphine. The reaction mixture containing phosphorus and indium precursors is heated to a temperature typically in excess of 200° C. to expedite formation of nanocrystals. A suitable temperature can be about 200° C., 210° C., or 220° C., or 230° C., or 240° C., or 250° C., or 260° C., or 270° C., or 280° C., or 290° C., or 300° C., or 310° C., or 320° C., or 330° C. The person of ordinary skill can ascertain whether a particular temperature is appropriate by monitoring to see if nanocrystals are formed. The indium precursor mixture can be heated prior to addition of the phosphorus precursor; alternatively, the phosphorus precursor mixture can be heated, prior to addition of the indium precursor to it. Alternatively, the mixture can be formed at a lower temperature and then heated to a desired temperature for the nanocrystal formation to occur.

In a preferred embodiment, the indium precursor in a suitable non-coordinating solvent is heated to a temperature between about 250° C. and 320° C., and the phosphorus precursor is added, either alone or in a solvent (e.g., a non-coordinating hydrocarbon, such as ODE). The phosphorus precursor may be preheated or not; typically, it is not, and is then added in one portion to the indium precursor to form a reaction mixture. The reaction mixture is then maintained at a desired temperature, and formation of nanocrystals is monitored by known methods. The user can determine when nanoparticles of a desired size have formed, as judged by the fluorescence emission wavelength of the nanoparticles, which correlates in a relatively well-understood manner with particle size. Once the desired particle size is obtained, the reaction can be stopped by cooling it down, or by adding a diluent, or both.

Preferably, the InP core nanocrystals are cleaned before they are used in a subsequent step to apply a shell. Solvents used to rinse or clean the nanocrystals should be carefully purified and dried and oxygen-free. The cores can be precipitated from the reaction mixture and collected by filtration or centrifugation, and separated from the bulk of the mixture. Then they can be rinsed with a solvent that does not dissolve them, also. For example, the reaction mixture can be diluted with acetonitrile and n-butanol, or with methanol, or mixtures of such solvents that form a miscible organic phase that is inhospitable to the lipophilic nanocrystals produced from the above reaction, and causes them to precipitate. The precipitated nanocrystals are collected and then rinsed with one or more solvents such as butanol or methanol or toluene or mixtures thereof. The nanocrystals can then be dissolved in a nonpolar, non-coordinating solvent such as hexanes.

Once clean, InP nanocrystal cores are obtained, they can be coated with a shell, such as ZnS. Since all residual indium and phosphorus has been removed during the purification process, such residual components are not available for incorporation into the shell (e.g., to form an alloy shell). The shelling step can involve preparing a lipophilic zinc salt by methods similar to those used to make the indium precursor described above. During the shell formation process, the InP cores are generally first contacted with the zinc source and then, subsequently contacted with the sulfur source. A zinc salt such as zinc acetate can be reacted with a lipophilic carboxylic acid compound, such as decanoic acid, octadecanoic acid, oleic acid, or the like in a non-coordinating solvent. Octadecene or other $C_{10}$-$C_{20}$ hydrocarbon solvents are often used for this step. Again, heating this mixture to a temperature over 150° C. and preferably above 200° C. results in exchange of the high molecular weight lipophilic carboxylate groups (e.g., oleate) for the zinc salt counterions (e.g., acetate), producing, e.g., a zinc dioleate plus acetic acid. The acetic acid is readily removed under the reaction conditions if the reaction temperature is above the boiling point of acetic acid (ca. 100° C.). Once the solution of a lipophilic zinc salt in a non-coordinating solvent has been prepared, it is cooled to a lower temperature, e.g., somewhere between about 50° C. and 150° C. Then a solution of the cleaned In P cores in a non-coordinating solvent (e.g., hexanes) is added, and the mixture is heated to a suitable temperature between about 200° C. and 320° C. to induce growth of a shell. When the desired temperature has been reached, a solution of a sulfur source (e.g., a sulfur precursor) is added to it. Preferably, the sulfur source is added slowly, i.e. over a time period of at least several minutes, rather than all at once. In some embodiments, the sulfur precursor is added to the heated reaction mixture containing zinc precursor (e.g., a lipophilic zinc salt) and InP cores over a period of at least 15 minutes, or over at least 30 minutes, or over about an hour or more. The combination of using a coordinating solvent during the shelling step and growing the outer shell very slowly results in a superior shell and superior overall characteristics (e.g., high quantum yield). Slow growth also can be useful for generating thick shells (e.g., 10 or more monolayers). In particular, slow addition of the sulfur source minimizes nucleation of zinc and sulfur precursors which can result in the formation of ZnS particles. In addition to contaminating the reaction mixture, the formation of ZnS particles can be additionally problematic, since ZnS is more likely to deposit on the ZnS byproduct particles than on partially formed InP/ZnS nanocrystals.

The sulfur source can be any suitable sulfur-containing material. This material can be a sulfur precursor. Representative sulfur sources include elemental sulfur, thiourea, or $TMS_2S$. The sulfur source can be dissolved in a medium that contains a coordinating solvent. In most cases, the medium does not contain a phosphine or phosphine oxide (e.g., TOP, TOPO, P(TMS)$_3$, and the like). Certain methods utilize an amine (e.g., oleylamine or another $C_5$-$C_{20}$ alkylamine) for this addition.

An exemplary method for preparing (e.g., growing) a ZnS shell on a nanocrystal core comprises dispersing the nanocrystal core in a hydrocarbon solvent to form a mixture; heating the mixture to a temperature above 200° C.; and slowly adding sulfur admixed with an alkylamine to the heated mixture.

In another exemplary embodiment, elemental sulfur is dissolved in an amine such as oleylamine and is added very slowly (over about an hour or more) to the heated mixture of InP cores and lipophilic zinc precursor in a non-coordinating solvent. After completion of the addition, the mixture is maintained at the desired temperature for a time period; then the reaction can be cooled and the InP core/ZnS shell nanocrystals (quantum dots) can be collected by standard methods, and can be cleaned as described above for nanocrystal cores. Due to the rigorous purification of the InP core, prior to the shell reaction, the ZnS shells produced by the methods described herein consist only of zinc and sulfur. Optionally, once the shell formation is completed, the reaction mixture can be cooled and a coordinating ligand such as TOP (trioctyl phosphine) can be added to produce a lipophilic coating on the freshly-made nanocrystals. In a preferred method, this is the first time the nanocrystals are treated with a coordinating phosphine ligand. Nanocrystals (quantum dots) made by this method exhibit higher quantum yields than those reported in the prior art, and are stable in storage.

The nanocrystals can be further treated with a surface coating, such as a hydrophilic polymer or an amphiphilic polymer coating, to improve their solubility in water or to render them water dispersible. Such coated nanocrystals can exhibit excellent stability in water. Alternatively, the nanocrystals can be treated with other types of coating materials, including, for example, dipeptides, thiol containing organic molecules (e.g. DHLA), phospholipids, hydrophilic phosphonic acids, or hydrophilic phosphine oligomers. Alternatively, they can be dispersed in a hydrophobic solvent such as hexanes without significant loss of quantum yield for a period of at least about 3 weeks. These nanocrystals can also be surface-modified in other ways, e.g. by PEGylation or conjugation to a bioaffinity molecule.

The following examples are included to illustrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Preparation of InP Core Nanocrystals

This describes an exemplary method for making InP nanocrystals. An InP core was prepared as follows. In a reaction flask under inert atmosphere, 0.88 g of indium acetate ($In(OAc)_3$), 0.254 g oleic acid, and 14.8 g of 1-octadecene (ODE) that was purified to remove oxygen and water were combined. The contents of the flask were heated to 260° C. while a flow of nitrogen was directed through the flask to remove acetic acid as it formed. After 5 minutes at this temperature, the flow of nitrogen was stopped. A 0.02 M solution of tris(trimethylsilyl)phosphine ($TMS_3P$) in ODE was prepared by adding 0.45 g of $TMS_3P$ to 7.101 g ODE. The contents of the flask were heated to 300° C. At 300° C., the $TMS_3P$ solution was quickly injected into the mixture. Nanocrystal formation was monitored by standard methods (achieving a desired fluorescence emission wavelength) until InP cores of the desired particle size was obtained, and the reaction was then cooled to room temperature.

The InP cores were washed by adding toluene, 1-butanol (BuOH) and acetonitrile to precipitate nanocrystal cores; all solvents were carefully dried to ensure they were anhydrous, and the operations were conducted under inert atmosphere. The mixture was centrifuged, and the pellet was collected. A small amount of toluene was added to the pellet, then BuOH was added, and the mixture was again centrifuged. The pellet was collected and was dispersed in hexanes.

Example 2

Addition of ZnS Shell to InP Core

The InP cores were treated as follows to grow a ZnS shell on the core. To a reaction flask under inert atmosphere, 4.3 mL ODE, 238.5 mg of oleic acid, and 77.5 mg zinc acetate ($Zn(OAc)_2$) were added. The mixture was heated to 260° C. and was then cooled to 80° C. While at 80° C., 4.9 mL of the washed InP cores prepared above, dispersed in n-hexanes, at an OD of 6.56, were added. The flask was placed under vacuum to remove hexane. The contents of the flask were then heated to 265° C. A 0.33 M solution of sulfur in oleylamine was prepared by adding 14.0 mg of sulfur to 1.04 g oleylamine. At 265° C. the sulfur solution was slowly added dropwise over a period of 75 minutes. After 75 minutes, 5.5 mL of trioctylphosphine (TOP) at room temperature was added to the reaction flask. The product is a population of quantum dots that are soluble in hydrophobic solvents (e.g., hexane, toluene, and the like) and stable for months. The product has an initially high quantum yield of about 50%, and loses less than 15% of its quantum yield when dissolved in hexanes or when modified by known methods to coat it with AMP and dispersed in water.

Example 3

Synthesis of Large InP Cores

To a 100 mL round bottom flask were added 2 mL of trioctylphosphine (TOP) and 100 nmol of purified InP cores in hexane from Example 1. The mixture was heated to 60° C. and a vacuum applied to remove hexane. In a second flask 0.141 g or anhydrous indium acetate, 0.410 g oleic acid, 12 mL of TOP, and 12 mL of 1-octadecene were added. The flask was heated under nitrogen to 250° C. and held there for a 5 minutes. The flask was allowed to cool to room temperature. The contents of the flask were loaded in to a syringe and mounted on a syringe pump. In an inert atmosphere glove box, 0.123 g of tris(trimethylsilyl)phosphine, 12 mL of TOP and 12 mL of ODE were mixed and loaded into a syringe. The syringe was removed from the glove box and loaded onto a second syringe pump. The core mixture was heated to 300° C. Once at 300° C., solutions from both syringe pumps were injected into the reaction flask at a rate of 33.6 µL per minute. After 8 hours the syringes pumps were stopped and reaction flask cooled. The final wavelength of the first absorbance feature for the large InP cores (6.2 nm) was 680 nm and the particle morphology, measured by a transition electron microscope, appeared generally spherical in shape.

Example 4

Addition of Thick ZnS Shell to InP Core

The following example describes a method for depositing thick ZnS shells on InP cores that uses a two monolayer by two monolayer addition process. The method involves first adding a quantity of zinc source such that, when a subsequent molar equivalent of sulfur is added, two monolayers (i.e., about 0.6 nm) of ZnS can form on the surface of the InP cores. The method can be adapted to different growth modes, as well, such as, for example, the growth mode could be, 1 monolayer by 1 monolayer, 3 monolayer by 3 monolayer, 4 monolayer by 4 monolayer, and so forth. The process also can use a mixture of modes in one process. In this example, a monolayer thickness was arbitrarily fixed to 3 angstroms. However, the thickness of a monolayer can be any value.

To 50 mL round bottom flask were added 11 mg (0.059 mmol) of anhydrous zinc acetate, 34 mg (0.118 mmol) of high purity oleic acid and 1 mL dioctylamine. This mixture was stirred and heated at 250° C. for 15 min, and then cooled to room temperature. Next, 80 nmol of InP cores (washed then dispersed in hexane as described in Example 1) and 0.6 mL dioctylamine were placed in another 50 mL flask and heated to 60° C. under vacuum. After complete removal of hexane, InP cores in dioctylamine were transferred to first flask containing a zinc precursor solution. The temperature was raised to 180° C. At 180° C., addition of 0.18 mL of a 0.33 M solution of elemental sulfur dissolved in ODE was initiated. The sulfur solution was added over the course of one hour by syringe pump. After the first drop of sulfur solution was added, the temperature was increased to 265° C. In a third flask, a 0.33 M zinc oleate solution was prepared by adding anhydrous zinc acetate and oleic acid to ODE in a molar ratio or 1:2. This solution was heated at 250° C. under a flow of nitrogen for 20 minutes then cooled to room temperature. After the first addition of sulfur was complete, 0.106 mmol of Zn-oleate from the third flask was quickly added into the reaction flask. Next an additional 0.106 mmol of S-ODE solution was injected over the course of two hours by syringe pump. This process was repeated until a total of twelve monolayers of ZnS were added. Before each two monolayer addition of shell, a new total surface area was calculated. InP nanocrystals with up to 20 monolayer (6 nm) or even thicker of ZnS shell could be synthesized using this procedure. InP nanocrystals with thick ZnS shell were purified using butanol and acetone at a ratio of dots:butanol:acetone 1:2:5. After centrifugation, the core shell nanocrystals were redispersed in hexane and precipitated with methanol at a volume ratio of 1:4. Purified dots were dispersed in hexane.

Example 5

Preparation of Dipeptide Coated InP/ZnS Nanocrystals

This example describes coating InP/ZnS nanoparticles with dipeptides to render the nanoparticles water dispersible. To 0.5 mL of the InP/ZnS core-shells from Example 2 were added 1 mL of isopropyl alcohol and 3 mL of methanol. The mixture was centrifuged, and the pellet was collected. To the pellet 2 mL of ethanol was added and pellet was collected again. Finally, 2 mL of hexane was added to make a clear, colored solution. To the hexane solution of nanoparticles, 1 mL of a mixture of 200 mM histidine-leucine and 100 mM glycine-histidine in 1 M sodium carbonate. The solution was heated at 72° C. for 15 minutes while mixing to allow the nanoparticles to partition into the aqueous phase. The hexane phase was removed by pipette followed by the addition of 2 mL of chloroform. Again, this mixture was heated to 72° C. for 1 hour while mixing. The aqueous layer was removed by pipette (~1 mL) and loaded into a 10,000 molecular weight cutoff dialysis cartridge (Pierce) and dialyzed against 375 mL of deionized water for 70 min. The contents of the dialysis cartridge were removed and glycerol was added to obtain a 5% by volume concentration. Next the pH was adjusted to 7.8 with 1 M 2-(N-morpholino)ethanesulfonic acid (MES) followed by the addition of tris(hydroxymethyl)phosphine (THP) to give a 5 mM concentration. This solution was stirred overnight at room temperature. Next histidine-leucine dipeptide was added to bring the final concentration up to 0.2 mM and the solution was stirred for 5 min. THP then was added to bring the final concentration up to 5 mM. This solution was stirred overnight at room temperature. Leucine was added to give a final concentration of 10 mM, and this solution was stirred overnight at room temperature. Nanoparticles were purified by ultrafiltration.

Example 6

Preparation of Dipeptide and PEG Coated InP/ZnS Nanocrystals

This example describes how to coat InP/ZnS nanoparticles with dipeptides and PEG to render the nanoparticles water dispersible. To 1.125 mL of the InP/ZnS core-shells from Example 2 were added 2.250 mL of butanol and 5 mL of acetone. The mixture was centrifuged, and the pellet was collected. 1.2 mL of hexane was added to the pellet to make a clear, colored solution. Finally, 2.5 mL of denatured ethanol was added. The mixture was centrifuged at 3000 rpm and the pellet was collected. To the pellet, 2 mL of hexane was added to the pellet. To 1 mL of the hexane solution of nanoparticles, 5 mL of 400 mM histidine in 1 M sodium carbonate, 16.5 mL of hexane, and 7 mL of butanol was added. The solution was heated at 73° C. for 30 minutes with mixing to allow the nanoparticles to partition into the aqueous phase. The hexane phase was removed by pipette followed by the addition of 17.5 mL of chloroform. This mixture was heated stirred for 10 minutes at room temperature. Next, 5 mL of deionized water was added and aqueous layer was removed. The aqueous layer was centrifuged at 4000 rpm for 5 minutes to remove large aggregates. Next the aqueous layer was loaded into a 10,000 molecular weight cutoff dialysis cartridge (Pierce) and dialyzed against 3.5 L of 25 mM sodium chloride solution for 70 min. After 70 min, the sodium chloride solution was replaces with 3.5 L of fresh 20 mM sodium chloride solution and dialyzed again for 70 min. The contents of the dialysis cartridge were removed (~16 mL) and a solution of 400 mM histidine-leucine and 200 mM glycine-histidine in 1 M sodium carbonate was added to obtain final concentration of 0.6 mM dipeptide. The mixture was stirred for 10 minutes followed by 1 minute of sonication. Next glycerol was added to make a final concentration of 5% by volume. Next the pH was adjusted to 8.5 with 1 M citric acid (MES) followed by the addition of tris(hydroxymethyl)phosphine (THP) to give a 5 mM concentration. This solution was stirred for 2 hours at room temperature. Next a bi-functional (amine, carbolylate) 1000 molecular weight (MW) polyethylene glycol (PEG) was added to a concentration of 0.3 mM and stirred for 5 min. Next a mono-functional (amine) 1000 MW PEG was added to a concentration of 0.7 mM and stirred overnight at room temperature. THP then was added to a concentration of 5 mM and stirred overnight. Next ethanolamine was added to a concentration of 10 mM and stirred overnight at room temperature. The nanoparticles were purified by ultrafiltration.

Example 7

Preparation of 4-Aminobenzophenone Treated Dipeptide and PEG Coated InP/ZnS Nanocrystals This example describes how to coat InP/ZnS nanoparticles with dipeptides and PEG and treat with 4-aminobenzophenone to render the nanoparticles water dispersible. To 2.2 mL of the InP/ZnS core-shells from Example 2 were added 4.4 mL of butanol and 11 mL of acetone. The mixture was centrifuged at 3000 rpm and the pellet was collected. To the pellet 80 mL of hexane was added to make a clear, colored solution. To the hexane solution of nanoparticles, 20 mL of a mixture of 200 mM histidine-leucine and 100 mM glycine-histidine in 1 M sodium carbonate and 28 mL of butanol was added. The solution was stirred overnight at room temperature to allow the nanoparticles to partition into the aqueous phase. The aqueous phase was removed by pipette and an additional 60 mL of deionized water was added. This was stirred to homogenize the mixture then concentrated to 10 mL by ultrafiltration. This solution was then loaded into a 10,000 molecular weight cutoff dialysis cartridge (Pierce) and dialyzed against 3.5 L of deionized water for 1.5 hours. The contents of the dialysis cartridge (~14.5 mL) were removed and placed into a 20 mL scintillation vial and stirred. Next a 10 mg/mL solution of 4-aminobenzophenone in DMSO was added to give a concentration of 0.5 mM. The solution was illuminated with a 365 nm UV lamp for 4 hours. Next the pH was adjusted to 9.0 with 1 M citric acid followed by the addition of tris (hydroxymethyl)phosphine (THP) to give a 5 mM concentration. This solution was stirred overnight at room temperature. Next a bi-functional (amine, carboxylate) 1000 MW PEG was added to a concentration of 300 µM followed by the addition of THP to a concentration of 5 mM. The solution was stirred overnight at room temperature. Additional THP was added to give a final concentration of 5 mM and the solution was stirred at room temperature for 4 hours. Glycine was added to give a final concentration of 30 mM and stirred overnight. The nanoparticles were purified by ultrafiltration with 50 mM borate at pH 8.3.

Example 8

Preparation of Bioconjugates to Dipeptide Coated Nanocrystals

This example describes preparation of a bioconjugate (e.g. streptavidin) to a dipeptide coated nanocrystal. To an aliquot of dipeptide coated InP/ZnS nanocrystals (e.g., prepared according to Example 3, 4, or 5), add sufficient carbodiimide (e.g 1-ethyl-3-[3-dimethylaminopropyl]carbodiimide hydrochloride (EDC) from Pierce) to partially or fully activate carbolylate functionality present on the surface to the nanoparticles. The carboxylate functionality can be associated with dipeptide molecules or the bi-functional PEG molecules on the surface of the nanoparticle. Once sufficient time has passed for the carbodiimide to activate the nanocrystals, any biomolecule containing amine or other sufficiently strong nucleophile can be added. Alternatively, the carbodiimide and biomolecule can be added together rather than sequentially. The mixture is stirred for a sufficient amount of time for all or some of the activated carboxylates to react with nucleophiles associated with the biomolecule to form a covalent bond (e.g., if the nucleophile is associated with the biomolecule is an amine, a covalent amide bond will be formed). Conjugates can be purified to remove unbound biomolecule and unreacted carbodiimide (e.g ultrafiltration, ultracentrifugation, tangential flow, and the like).

Example 9

Preparation of Water-Dispersible InP/ZnS Nanocrystals Using Hydrophobically Modified Hydrophilic Polymers Hydrophobic quantum dots were dispersed in an aqueous solvent system using hydrophobic ally modified hydrophilic polymers as described in U.S. Pat. No. 6,649,138. Two milliliters of hydrophobically coated InP/ZnS nanocrystals (10-20 μM), prepared in Example 2, were precipitated with a mixture of 4 mL of butanol and 10 mL of acetone. The flocculate was centrifuged at 3000 rpm for 3 minutes to form a pellet of the nanocrystals. The pellet was redispersed with 2 mL of hexane. To the hexane solution, 4 mL of denatured ethanol was added. The flocculate was centrifuged at 3000 rpm for 3 minutes to form a pellet of nanocrystals. Two milliliters of chloroform was added to the nanocrystal pellet to yield a freely dispersed solution. 81.5 milligrams of the hydrophobically modified poly(acrylic acid) was dissolved in 2 mL of chloroform. Sodium hydroxide (1.0 M in methanol) was added to the polymer solution to raise the solution to pH 8 (pH was measured by spotting a small aliquot of the chloroform solution on pH paper, evaporating the solvent and thereafter wetting the pH paper with distilled water). Thereafter the polymer solution was added to 2 mL of chloroform in a 25 mL round bottom flask. The solution was stirred for 1 minute to ensure complete admixture of the polymer solution. With continued stiffing the washed nanocrystal dispersion described above was added dropwise to the polymer solution. The dispersion was then stirred for two minutes to ensure complete mixing of the components and thereafter the chloroform was removed under vacuum with low heat to yield a thin film of the particle-polymer complex on the wall of the flask. Two milliliters of 50 mM borate solution (pH 9.0) were added to the flask and swirled along the walls of the flask to aid in dispersing the particles in the aqueous medium. The dispersion was then allowed to stir overnight at room temperature. At this point the nanocrystals were freely dispersed in the aqueous medium.

Example 10

Preparation of Polyethoxylated Modified Water Dispersible Quantum Dots

Water dispersible quantum dots from Example 9 are mixed with a 7000 fold molar excess of polyethylene glycol (PEG) molecules. PEG molecules or mixtures of PEG molecules ranging in molecular weight from 200 to 20,000 Da and having various functionalities such as methoxy, hydroxyl, amine, carboxy, phosphate, thiol, azido, NHS ester, aldehyde, isocyanate, and biotin can be used. Next, a 3000 fold molar excess of EDC is added and the mixture was stirred for two hours. Excess PEG and EDC were removed by ultrafiltration.

Example 11

Preparation of Quantum Dot Streptavidin Conjugates

To polyethoxylated modified water dispersible quantum dots from Example 10, a 100 fold molar excess of bis(sulfosuccinimidyl)suberate (BS3) was added and gently mixed for 30 minutes. Excess BS3 was removed via purified over an ILLUSTRA NAP-5 column (GE Healthcare). Purified BS3 activated particles from the NAP-5 column were mixed with a 40 fold molar excess or streptavidin and allowed to incubate at room temperature for 2 hours. Remaining unreacted BS3 was quenched with a 1 M solution of glycine. A certain volume of 1 M glycine solution was added to the streptavidin conjugated particles such that the solution contained 50 millimoles of glycine per liter of solution. The conjugates were purified from excess glycine by ultrafiltration.

Example 12

Preparation of Quantum Dot Secondary Antibody Conjugates

To polyethoxylated modified water dispersible quantum dots from Example 10, a 130 fold molar excess of succinimidyl-4-(N-maleimidomethyl)cyclohexane-1-carboxylate (SMCC) was added. This solution was gently mixed and incubated at room temperature for 1 hour. SMCC activated quantum dots were purified from excess SMCC over an ILLUSTRA NAP-25 column. In a second reaction container, 0.35 mg of Fab or F(ab')2 antibody fragments per nanomole of polyethoxylated particles were mixed with 4000 nanomoles of dithiothreitol (DTT) per milligram of antibody and gently mixed for 30 minutes. DTT reduced antibody was purified from excess DTT over an illustra NAP-25 column. Activated quantum dots and reduced antibody were mixed and allowed to incubate at room temperature for 2 hours. Remaining unreacted SMCC was quenched by incubating conjugates for 30 minutes with a 45 fold molar excess of 2-mercaptoethanol. Antibody conjugates were purified by fast protein liquid chromatography (FPLC).

All of the compositions and/or methods and/or processes and/or apparatus disclosed and claimed herein can be made and executed without undue experimentation in light of the present disclosure. While the compositions and methods provided herein have been described in terms of preferred embodiments, it will be apparent to those of skill in the art that variations may be applied to the compositions and/or methods and/or apparatus and/or processes and in the steps or in the sequence of steps of the methods described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

The invention claimed is:

1. A method of detecting a target in a sample, the method comprising:

contacting a biological sample with a population of water-dispersible semiconductor nanocrystals in an aqueous medium, wherein each nanocrystal comprises a core consisting essentially of indium and phosphorus, and a shell consisting essentially of zinc and sulfur, wherein the shell is directly on the surface of the core, wherein the quantum yield of the semiconductor nanocrystals when dispersed in the aqueous medium is at least 35%, and wherein the population of nanocrystals is non-toxic to cells or tissues; and detecting the fluorescence emission of the population of semiconductor nanocrystals.

2. A method of detecting an interaction between a compound and a biological target, comprising:

providing a non-toxic composition capable of a characteristic spectral emission, the composition comprising a compound and a water-dispersible semiconductor nanocrystal in an aqueous medium, wherein each nanocrystal comprises a core consisting essentially of indium and phosphorus, and a shell consisting essentially of zinc and sulfur, wherein the shell is directly on the surface of the core, wherein the semiconductor nanocrystal is associated with the compound, wherein the composition in the aqueous medium has a quantum yield of at least 35% and is non-toxic to cells or tissues;

allowing a sample comprising a biological target to interact with the composition; and detecting interaction between the compound and the biological target by monitoring the spectral emission of the sample, wherein the emission of the semiconductor nanocrystal provides information about a biological state or event.

3. The method of claim 1, wherein each semiconductor nanocrystal further comprises a surface layer on the shell, wherein the layer comprises an alkyl carboxylic acid or salt thereof.

4. The method of claim 1, wherein each semiconductor nanocrystal further comprises a surface layer on the shell that comprises a $C_4$-$C_{20}$ fatty acid.

5. The method of claim 1, wherein each semiconductor nanocrystal further comprises a surface layer on the shell that comprises a $C_5$-$C_{20}$ alkylamine.

6. The method of claim 1, wherein each semiconductor nanocrystal further comprises a water-stabilizing layer on the shell that renders the nanocrystal water-dispersible.

7. The method of claim 1, wherein the thickness of the ZnS shell is at least 0.5 nm.

8. The method of claim 1, wherein the shell comprises 5-30 monolayers of ZnS.

9. The method of claim 2, wherein the semiconductor nanocrystal further comprises a water-stabilizing layer that renders the nanocrystal dispersible in the aqueous medium.

10. The method of claim 1 or 2, wherein the core consists of indium and phosphorus.

11. The method of claim 10, wherein the core does not include zinc.

* * * * *